United States Patent
Yamamoto et al.

(10) Patent No.: US 9,855,261 B2
(45) Date of Patent: Jan. 2, 2018

(54) POLYMERIC COMPOUND HAVING CAMPTOTHECIN COMPOUND AND ANTI-CANCER EFFECT ENHANCER BOUND THERETO, AND USE OF SAME

(71) Applicant: Nippon Kayaku Kabushiki Kaisha, Chiyoda-ku, Tokyo (JP)

(72) Inventors: Keiichiro Yamamoto, Tokyo (JP); Manami Okazaki, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/440,090

(22) PCT Filed: Oct. 31, 2013

(86) PCT No.: PCT/JP2013/079551
§ 371 (c)(1),
(2) Date: May 1, 2015

(87) PCT Pub. No.: WO2014/073447
PCT Pub. Date: May 15, 2014

(65) Prior Publication Data
US 2015/0290185 A1    Oct. 15, 2015

(30) Foreign Application Priority Data

Nov. 8, 2012 (JP) .................................. 2012-246037

(51) Int. Cl.
| | |
|---|---|
| A61K 31/4745 | (2006.01) |
| A61K 31/551 | (2006.01) |
| A61K 31/55 | (2006.01) |
| A61K 31/765 | (2006.01) |
| A61K 31/4184 | (2006.01) |
| A61K 47/48 | (2006.01) |

(52) U.S. Cl.
CPC ...... *A61K 31/4745* (2013.01); *A61K 31/4184* (2013.01); *A61K 31/55* (2013.01); *A61K 31/551* (2013.01); *A61K 31/765* (2013.01); *A61K 47/48215* (2013.01); *A61K 47/48315* (2013.01)

(58) Field of Classification Search
CPC ............ A61K 31/4184; A61K 31/4745; A61K 31/55; A61K 31/551; A61K 31/765; A61K 47/60; A61K 47/645
See application file for complete search history.

(56) References Cited

U.S. PATENT DOCUMENTS

| | | |
|---|---|---|
| 7,429,578 B2 | 9/2008 | Webber et al. |
| 7,495,099 B2 | 2/2009 | Kitagawa et al. |
| 7,700,709 B2 | 4/2010 | Masuda et al. |
| 8,808,749 B2 | 8/2014 | Kitagawa et al. |
| 8,920,788 B2 | 12/2014 | Kitagawa et al. |
| 8,999,987 B2 | 4/2015 | Wang et al. |
| 9,018,323 B2 | 4/2015 | Yamamoto et al. |
| 2008/0248097 A1 | 10/2008 | Kwon et al. |
| 2012/0116051 A1* | 5/2012 | Kitagawa ............. A61K 31/167 530/323 |

FOREIGN PATENT DOCUMENTS

| | | |
|---|---|---|
| CN | 1708540 A | 12/2005 |
| EP | 1580216 A1 | 9/2005 |
| EP | 2204398 A1 | 7/2010 |
| JP | 2010-519305 A | 6/2010 |

(Continued)

OTHER PUBLICATIONS

Miknyoczki Molecular Cancer Therap. p. 371 2003.*
International Search Report and Written Opinion dated Nov. 26, 2013 in corresponding PCT application No. PCT/JP2013/079551.
International Preliminary Report on Patentability dated May 12, 2015 in corresponding PCT application No. PCT/JP2013/079551.

(Continued)

*Primary Examiner* — Suzanne Ziska
*Assistant Examiner* — Thurman Wheeler
(74) *Attorney, Agent, or Firm* — Nields, Lemack & Frame, LLC

(57) ABSTRACT

The purpose of the present invention is to provide a polymeric compound in which a camptothecin compound and an anti-cancer effect enhancer, particularly a PARP inhibitor, are bound to a single molecule, whereby it becomes possible to reduce the toxicity to normal cells and deliver and release the two components to an affected area with high efficiency to thereby improve the pharmacological efficacy of the two components. Provided is a polymeric compound represented by general formula (1).

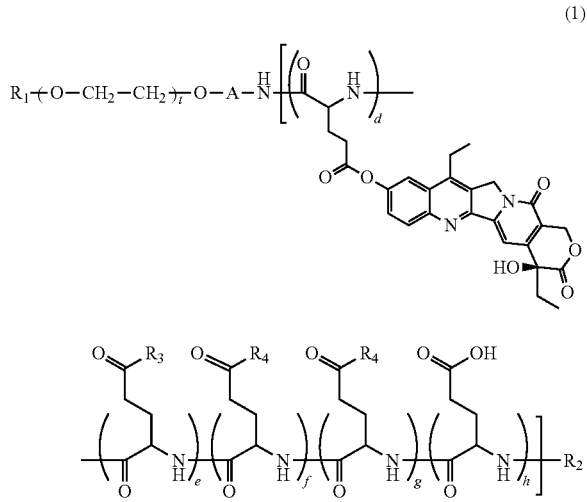

5 Claims, 3 Drawing Sheets

(56) References Cited

FOREIGN PATENT DOCUMENTS

| WO | 00/42040 A1 | 7/2000 |
| WO | 2004/039869 A1 | 5/2004 |
| WO | 2006/120914 A1 | 11/2006 |
| WO | 2009/116509 A1 | 9/2009 |
| WO | 2009/142328 A1 | 11/2009 |
| WO | 2010/017055 A2 | 2/2010 |
| WO | 2010/131675 A1 | 11/2010 |
| WO | 2012/067138 A1 | 5/2012 |

OTHER PUBLICATIONS

Advanced Drug Delivery Reviews, 2009, vol. 61 (10), pp. 768-784, "Intelligent polymeric micelles from functional poly (ethylene glycol)-poly(amino acid) block copolymers", Bae, et al.

J. Med. Chem., 2008, vol. 51, pp. 6581-6591, "4-[3-(4-Cyclopropanecarbonylpiperazine-l-carbonyl)-4-fluorobenzayl]-2H-phthalazin-1-one: A Novel Bioavailable Inhibitor of Poly(ADP-ribose) Polymerase-1", Menear, et al.

Parp Inhibitor ABT-888 as Potentiating Agent for Topoisomerase Inhibitor SN-38, Masters Thesis, Graduate School—New Brunswick, Rutgers, The State University of New Jersey and The Graduate School of Biomedical Sciences/University of Medicine and Dentistry of New Jersey, May 2009, 59 pages, Sohail, et al.

J. Med. Chem., 2000, vol. 43, pp. 4084-4097, "Resistance-Modifying Agents.9.1 Synthesis and Biological Properties of Benzimidazole Inhibitors of the DNA Repair Enzyme Poly(ADP-ribose) Polymerase", White, et al.

European communication dated May 11, 2016 in corresponding European patent application No. 13853624.8.

Taiwanese communication, with English translation, dated Feb. 3, 2017 in corresponding Taiwanese patent application No. 102140567.

Toyoda et al., Japanese Journal of Cancer and Chemotherapy, Apr. 2012, 39 (4), pp. 519-524.

Japanese communication, with English translation, dated Jul. 11, 2017 in corresponding Japanese patent application No. 2014-545671.

* cited by examiner

POLYMERIC COMPOUND HAVING CAMPTOTHECIN COMPOUND AND ANTI-CANCER EFFECT ENHANCER BOUND THERETO, AND USE OF SAME

TECHNICAL FIELD

The present invention relates to a polymeric compound in which a camptothecin compound and an anti-cancer (anti-tumor) effect enhancer are bound to a single molecule. The polymeric compound as disclosed herein can be used for delivering various plural drugs to an affected site.

BACKGROUND ART

Camptothecin is a vegetable alkaloid contained in plants such as *Camptotheca acuminata* of Chinese origin and a type I topoisomerase inhibitor. This selectively binds to the type I topoisomerase which forms a complex with DNA to stabilize its structure. As a result, it prevents the recombination of the cleaved DNA, and leads to the stop of the synthesis of DNA, thereby inducing the death of cells.

Camptothecin exhibits a high anti-tumor effect, and an anticancer agent of it had been developed in the 1960s. However, it was shown to have a strong toxicity causing bone-marrow suppression and hemorrhagic cystitis, and therefore its clinical test had been discontinued.

After that, topotecan and irinotecan had been developed as derivatives of camptothecin which have a better solubility in water, a stronger anti-tumor activity and a lower toxicity than those of camptothecin.

Topotecan exhibits its anti-tumor effect without metabolism, and 20-40% of its dose is excreted renally. Therefore, diarrhea which is its side effect is mild.

Irinotecan per se has an anti-tumor effect. It is metabolized in vivo by carboxyesterase to form a more active metabolite, 7-ethyl-10-hydroxycamptothecin (hereinafter, referred to as EHC), said metabolite exhibits a stronger anti-tumor effect. Moreover, the ratio of irinotecan and EHC in the form of lactone, which is biologically active, in plasma is higher than that of topotecan, and irinotecan and EHC has a long half-life.

The camptothecin derivatives are used for the treatment of many types of cancers in clinical use. Topotecan has been approved for the treatment of small cell lung cancer and the treatment of ovarian cancer pretreated with cancer chemotherapeutic agent(s). Irinotecan has been approved for the treatment of wide cancers, i.e., small cell lung cancer, non-small cell lung cancer, cervical cancer, ovarian cancer, stomach cancer (inoperable or recurrent), colon-rectal cancer (inoperable or recurrent), breast cancer (inoperable or recurrent), squamous cell cancer, and lymphatic malignancy (non-Hodgkin's lymphoma).

As one of camptothecin derivatives, Patent Literature 1 discloses a camptothecin derivative conjugated to a polymer. This polymer conjugate is obtained by ester binding a phenolic camptothecin compound to a copolymer of polyethylene glycol and a polymer having a side chain of carboxy group. The polymer conjugate has an in vivo sustained-release property and an excellent therapeutic effect on the basis of the binding of camptothecin compound via phenyl ester linkage which can be easily chemically cleaved. Further, the polymer conjugate forms a micelle and has an efficacy selective to tumors. It is expected to have a less side effect. Moreover, the polymer conjugate can release camptothecin compound without depending on enzyme(s).

This suggests that the therapeutic effect of the polymer conjugate is not likely to be affected by the individual differences among patients.

Poly(ADP-ribose)polymerase (PARP) is the enzyme catalyzing polyADP-ribosyl action that adding ADP ribose residue to proteins by using oxidative NAD (nicotinamide adenine dinucleotide) as a substrate to polymerize them. PARP senses the cleavage of single-stranded DNA, and then repairs DNA.

A PARP inhibitor competitively inhibits oxidative NAD when PARP recognizes oxidative NAD and repairs DNA, thereby exhibiting a pharmacological effect. That is, the PARP inhibitor inhibits PARP to cleave single-stranded DNA in tumor cells and to further cleave double-stranded DNA that is important for survival of the cells, leading to the death of the tumor cells.

In particular, in BRCA (Breast Cancer Susceptibility Gene)-mutant breast cancer, which is representative of hereditary breast cancer, inhibiting PARP which acts in the complement pathway of repair pathway of DNA leads to anti-tumor effect. In normal cells, even if PARP is inhibited, the cleavage of double-stranded DNA is repaired via the mechanism of repairing DNA by BRCA, resulting in no death of the cells. In contrast, in the tumor cells having BRCA mutation, the mechanism of repairing DNA does not act by the inhibition of PARP, and non-repaired single-stranded DNA accumulates in the cells, resulting in the cleavage of double-stranded DNA and the death of the tumor cells.

PARP plays an important role of the recognition of damage of DNA and the repairing it. Therefore, it is assumed that its inhibitor becomes an enhancer of the effect of anticancer agent having the effect of damaging DNA. With expectation of possibility of enhancing the effect by combining the PARP inhibitor with an anticancer agent such as temozolomide, carboplatin or gemcitabine, the treatment of cancers using PARP inhibitor has been currently developed.

The treatment of BRCA1- or BRCA2-mutant tumor by the combination of a PARP inhibitor, olaparib, with other anticancer agents (e.g. carboplatin and gemcitabine etc.) shows better results.

A rucaparib derivative, AG014699, which is a PARP inhibitor, is combined with temozolomide in the treatment of cancers, resulting in good tolerability and good anti-cancer effect.

Furthermore, the results of phase II clinical trial of combination of a PARP inhibitor, veliparib (ABT-888) with temozolomide shows that the combination exhibits the effect on metastatic breast cancer, and has good tolerability, suggesting that the combination may be a promising treatment method.

Patent Literature 1 discloses a polymeric compound to which a single drug having phenolic hydroxy group is bound. Patent Literature 2 discloses a polymeric compound to which a single drug having an alcoholic hydroxy group is bound. Patent Literature 3 and Non-Patent Literature 1 disclose the administration of the combination of a PARP inhibitor with a low-molecular anticancer agent such as temozolomide, carboplatin or gemcitabine, and a polymeric compound to which doxorubicin and other anticancer agents etc. are bound.

However, a polymeric compound in which camptothecin compound and an anti-cancer effect enhancer, for example, a PARP inhibitor are bound to a single molecule is not known.

CITATION LIST

Patent Literature

Patent Literature 1: WO 2004/039869
Patent Literature 2: WO 2010/131675
Patent Literature 3: JP 2010-519305 A

Non-Patent Literature

Non-Patent Literature 1: Younsoo Bae & Kazunori Kataoka, Adv. Drug Deliv. Rev., 61, 768-784 (2009)

SUMMARY OF THE INVENTION

Problems to be Solved by the Invention

The purpose of the present invention is to provide a polymeric compound in which a camptothecin compound and anti-cancer effect enhancer, in particular, a PARP inhibitor are bound to a single molecule, whereby it becomes possible to reduce the toxicity to normal cells and deliver and release the two components to an affected site with high efficiency to thereby improve the pharmacological efficacy of the two components.

Means for Solving the Problems

The inventors of the invention have created a polymeric compound in which a camptothecin compound and anti-cancer effect enhancer, in particular a PARP inhibitor are bound to a single molecule, have found that said compound has a therapeutic effect which is sufficient for a chemotherapeutic agent, and achieved the invention.

Specifically, the invention relates to the following 1) to 12).

1) A polymeric compound represented by the following general formula (1):

wherein $R_1$ represents (C1-C4) alkyl group which may optionally have a substituent;

t represents an integer of 45-450;

A represents (C1-C6)alkylene group;

d+e+f+g+h represents an integer of 6-60;

the ratio of d compared to d+e+f+g+h is 5-50%:

the ratio of e compared to d+e+f+g+h is 5-90%;

the ratio of f compared to d+e+f+g+h is 0-90%, the ratio of g compared to d+e+f+g+h is 0-90%;

the ratio of h compared to d+e+f+g+h is 0-90%;

$R_2$ represents hydrogen atom or (C1-C4)acyl group;

$R_3$ represents a residue of anti-cancer effect enhancer, or an aspartic acid residue to which the anti-cancer effect enhancer is bound;

$R_4$ represents an aspartic acid residue and/or an aspartic acid imide residue;

$R_5$ represents $N(R_6)CONH(R_7)$; and $R_6$ and $R_7$, which may be the same or different from each other, represent (C3-C6)branched or cyclic alkyl group, or (C1-C5)branched or linear alkyl group which may be substituted with a tertiary amino group.

2) The polymeric compound described in the above 1), wherein $R_1$ is methyl or ethyl group;

A is ethylene or trimethylene group;

$R_2$ is acetyl or propionyl group;

both $R_6$ and $R_7$ are cyclohexyl or isopropyl group;

the ratio of d compared to d+e+f+g+h is 5-40%;

the ratio of e compared to d+e+f+g+h is 5-80%;

the ratio of f compared to d+e+f+g+h is 0-60%;

the ratio of g compared to d+e+f+g+h is 5-40%;

the ratio of h compared to d+e+f+g+h is 0-30%.

[Chemical Formula 1]

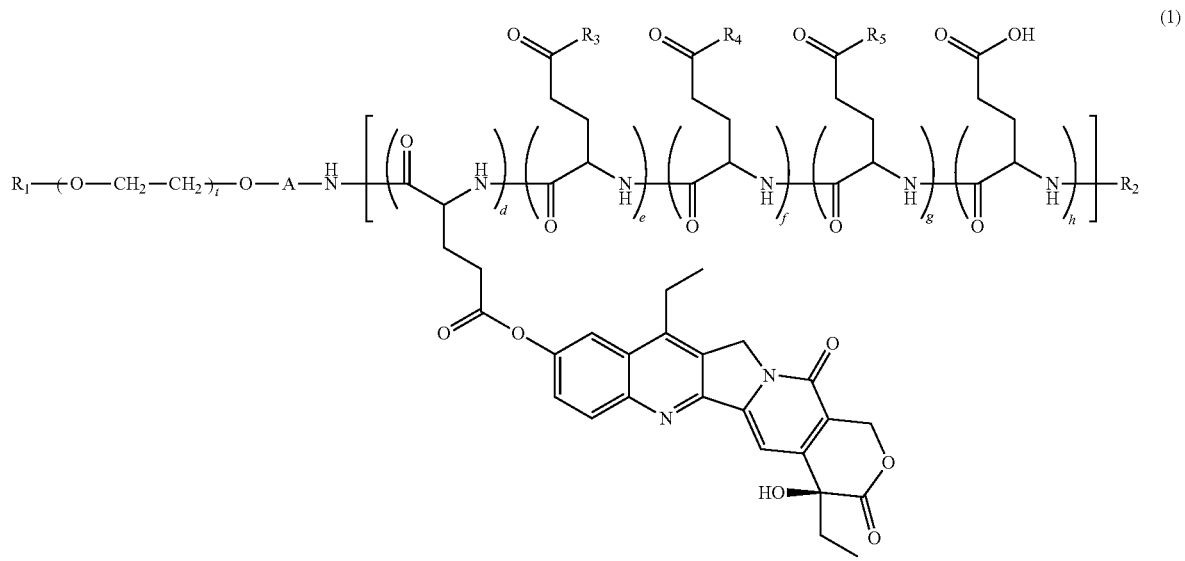

3) The polymeric compound described in the above 1) or 2), wherein $R_3$ is the following general formula (2) or (3):

[Chemical Formula 2]

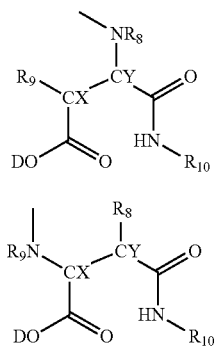

(2)

(3)

in which $R_8$ and $R_9$ each independently represent a hydrogen atom or (C1-C6)alkyl group which may have a substituent;

$R_{10}$ represents hydrogen atom, (C1-C40)alkyl group which may have a substituent, (C1-C40)aralkyl group which may have a substituent, an aromatic group which may have a substituent, or an amino acid residue having a protected carboxy group;

CX—CY represents CH—CH or C═C (double bond),

OD (O represents oxygen atom) represents a residue of anti-cancer effect enhancer.

4) The polymeric compound described in the above 3), wherein $R_4$ is selected from the group consisting of substituents represented by the following general formulae (4), (5) and (6):

[Chemical Formula 3]

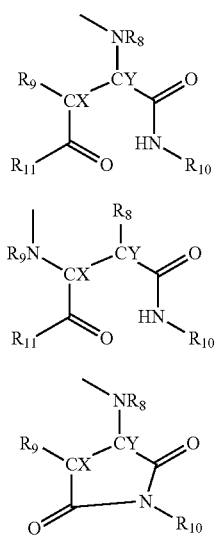

(4)

(5)

(6)

in which $R_8$, $R_9$, $R_{10}$ and CX—CY have the same meanings as above;

$R_{11}$ represents hydroxy group or $N(R_{12})CONH(R_{10})$; and $R_{12}$ and $R_{13}$, which may be the same or different from each other, represent (C3-C6)branched or cyclic alkyl group, or (C1-C5)branched or linear alkyl group which may be substituted with a tertiary amino group.

5) The polymeric compound described in the above 3) or 4), wherein both $R_8$ and $R_9$ are hydrogen atom;

CX—CY is CH—CH; and $R_{10}$ is phenylbutyl group.

6) The polymeric compound according to anyone of the above 1)-5), wherein the anti-cancer effect enhancer is a PARP inhibitor.

7) The polymeric compound according to anyone of the above 1)-5), wherein the anti-cancer effect enhancer is a PARP inhibitor having a phenolic hydroxy group.

8) The polymeric compound according to anyone of the above 3)-5), wherein the anti-cancer effect enhancer is a PARP inhibitor having an alcoholic hydroxy group.

9) The polymeric compound described in the above 6), wherein the PARP inhibitor is at least one selected from the group consisting of a 1H-benzimidazole-4-carboxamide derivative, an olaparib derivative, a rucaparib derivative and a BMN673 (5-Fluoro-8(S)-(4-fluorophenyl)-9(R)-(1-methyl-1H-1,2,4-triazol-5-yl)-3,7,8,9-tetrahydro-2H-pyrido[4,3,2-de]phthalazin-3-one) derivative.

10) The polymeric compound according to any one of the above 6), 7) or 9), wherein the PARP inhibitor is 2-(4-hydroxyphenyl)-1H-benzimidazole-4-carboxamide or 2-(4'-hydroxyphenyl)-3,4,5,6-tetrahydro-1H-azepino[5,4,3-cd]indol-6-one.

11) The polymeric compound according to any one of the above 6), 8) or 9), wherein the PARP inhibitor is 2-(4'-hydroxymethylphenyl)-3,4,5,6-tetrahydro-1H-azepino[5,4,3-cd]indol-6-one or 4-[4-fluoro-3-([1,4]diazepane-1-carbonyl-4-hydroxyethyl)benzyl]-2H-phthalazin-1-one.

12) An anticancer agent comprising the polymeric compound according to anyone of the above 1)-11) as an active ingredient.

Effects of the Invention

The polymeric compound of the invention is characterized in that EHC, which is a key drug of cancer therapy, camptothecin compound, and an anti-cancer effect enhancer, in particular, a PARP inhibitor are bound to a single molecule. Said polymeric compound is a drug delivery system capable of controlling their doses and their release rates, and can deliver the drugs to an affected site simultaneously. Therefore, said polymeric compound has an improved anti-cancer effect and a lower side effect, and can achieve an effective and safe cancer chemotherapy.

MODE FOR CARRYING OUT THE INVENTION

Figure 1:
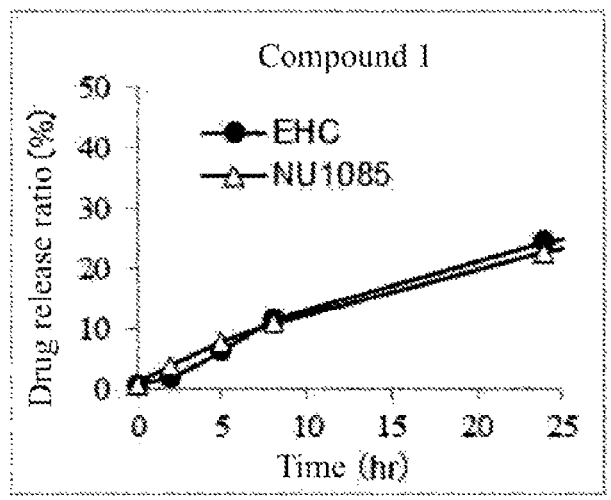
FIG. 1 illustrates the ratio of the amount of EHC and PARP inhibitor (NU1085) released from Compound 1 to the total amounts of bound drug in PBS solution (phosphate buffered physiological saline; pH 7.1) at 37° C.
Figure 2:
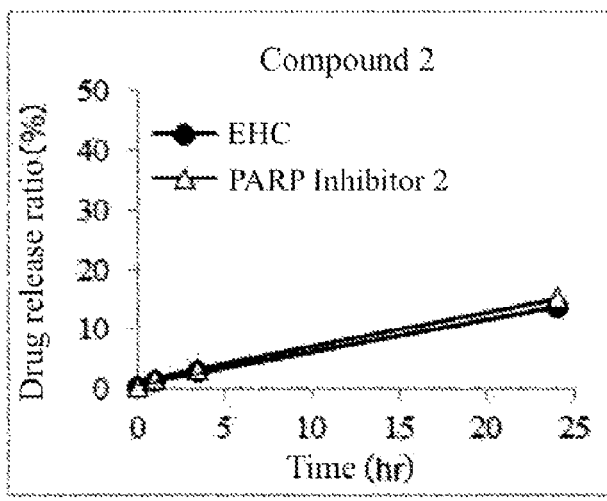
FIG. 2 illustrates the ratio of the amount of EHC and PARP inhibitor 2 released from Compound 2 to the total amounts of bound drug in PBS solution (phosphate buffered physiological saline; pH 7.1) at 37° C.
Figure 3:
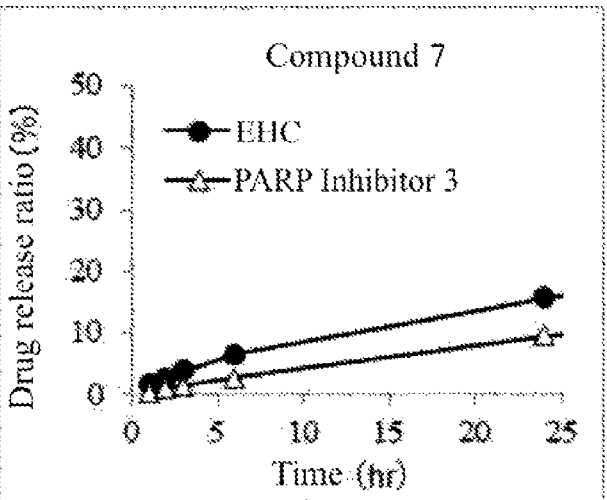
FIG. 3 illustrates the ratio of the amount of EHC and PARP inhibitor 3 released from Compound 7 to the total amounts of bound drug in PBS solution (phosphate buffered physiological saline; pH 7.1) at 37° C.
Figure 4:
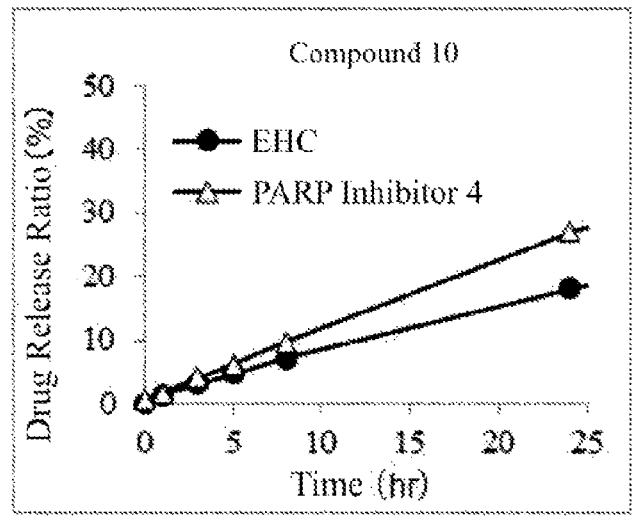
FIG. 4 illustrates the ratio of the amount of EHC and PARP inhibitor 4 released from Compound 10 to the total amounts of bound drug in PBS solution (phosphate buffered physiological saline; pH 7.1) at 37° C.
Figure 5:
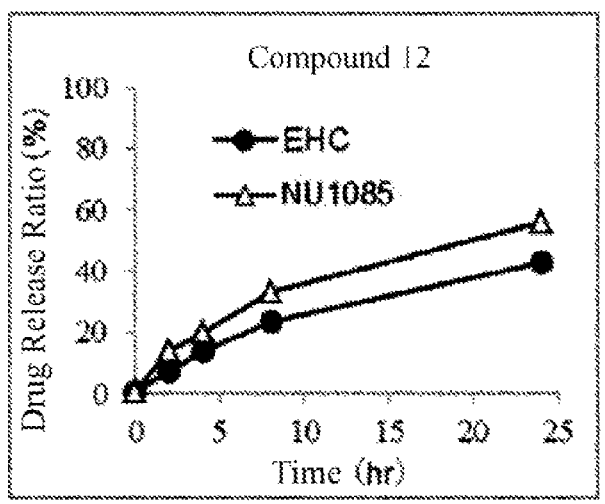
FIG. 5 illustrates the ratio of the amount of EHC and PARP inhibitor (NU1085) released from Compound 12 to the total amounts of bound drug in PBS solution (phosphate buffered physiological saline; pH 7.1) at 37° C.
Figure 6:
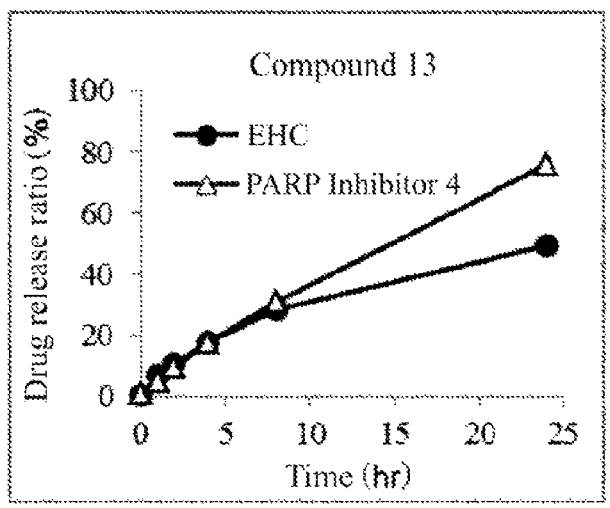
FIG. 6 illustrates the ratio of the amount of EHC and PARP inhibitor 4 released from Compound 13 to the total amounts of bound drug in PBS solution (phosphate buffered physiological saline; pH 7.1) at 37° C.

The polymeric compound of the invention, in which a camptothecin compound and anti-cancer effect enhancer are bound to a single molecule, is a block copolymer of a polyethylene glycol structural moiety and a polyglutamic acid structural moiety to which a drug etc. are linked. Said polymeric compound is represented by said general formula (1) wherein $R_1$ represents (C1-C4) alkyl group which may optionally have a substituent;

t represents an integer of 45-450;

A represents (C1-C6)alkylene group;

d+e+f+g+h represents an integer of 6-60;

the ratio of d compared to d+e+f+g+h is 5-50%:

the ratio of e compared to d+e+f+g+h is 5-90%;

the ratio of f compared to d+e+f+g+h is 0-90%, the ratio of g compared to d+e+f+g+h is 0-90%;

the ratio of h compared to d+e+f+g+h is 0-90%;

$R_2$ represents hydrogen atom or (C1-C4)acyl group;

$R_3$ represents a residue of anti-cancer effect enhancer, or an aspartic acid residue to which the anti-cancer effect enhancer is bound;

$R_4$ represents an aspartic acid residue and/or an aspartic acid imide residue;

$R_5$ represents $N(R_6)CONH(R_7)$; and $R_6$ and $R_7$, which may be the same or different from each other, represent (C3-C6)branched or cyclic alkyl group, or (C1-C5)branched or linear alkyl group which may be substituted with a tertiary amino group.

Examples of the (C1-C4)alkyl group of $R_1$ of general formula (1) include methyl, ethyl, propyl, isopropyl, n-butyl, isobutyl, sec-butyl and tert-butyl groups. Examples of the substituent of (C1-C4)alkyl group which have a substituent include amino, dialkylamino, alkyloxy, carboxy groups and the like. $R_1$ is preferably methyl or ethyl group, particularly preferably methyl group.

The symbol "t" in the general formula (1) is 45-450, preferably 90-340.

The group "A" in the general formula (1), which is a group linking a polyethylene glycol structural moiety and a polyglutamic acid structural moiety, represents (C1-C6) alkylene group, for example, such as methylene, ethylene, trimethylene, tetramethylene, hexamethylene or the like. Among these, ethylene or trimethylene group is preferable, and trimethylene group is particularly preferable.

The polyglutamic acid structural moiety of the polymeric compound of the invention represented by the general formula (1) has the structure of glutamic acid units thorough the α-amino acid groups. Each glutamic acid unit may be either L- or D-type. The total number of glutamic acid units in the general formula (1), i.e. d+e+f+g+h is 6-60, preferably 8-40. Thus, the average molecular weight of polyglutamic acid structural moiety is about 600-15000, preferably about 800-10000.

$R_2$ in the general formula (1) can be hydrogen atom or (C1-C4)acyl group. $R_2$ is preferably (C1-C4)acyl group, such as, for example, formyl, acetyl, propionyl group or the like. Among these, acetyl or propionyl group is preferably, and acetyl group is particularly preferable.

$R_5$ in the general formula (1) represents $N(R_6)CONH(R_7)$. $R_6$ and $R_7$, which may be the same or different from each other, represent (C3-C6)branched or cyclic alkyl group or (C1-C5)branched or linear alkyl group which may be substituted by a tertiary amino group. Examples of said (C3-C6)branched or cyclic alkyl group include isopropyl, isobutyl, sec-butyl, tert-butyl, 1-methylbutyl, 2-methylbutyl, neopentyl, cyclohexyl groups and the like. Preferably, said (C3-C6) branched or cyclic alkyl group is isopropyl or cyclohexyl group. Examples of said (C1-C5) branched or linear alkyl group which may be substituted by a tertiary amino group include ethyl, dimethylaminopropyl groups and the like.

As shown in the general formula (1), the hydroxy group at position 10 of EHC, which is a camptothecin derivative, is ester-bound to carboxy group of a side chain of polyglutamic acid structural moiety of the polymeric compound of the invention.

$R_3$ in the general formula (1) represents an anti-cancer effect enhancer residue, or an aspartic acid residue to which anti-cancer effect enhancer is bound. The anti-cancer effect enhancer in the invention is a drug administered for mainly enhancing an effect of anticancer agent thorough various effect mechanisms. Examples of the anti-cancer effect enhancer include PARP inhibitors, flavonoid derivatives and the like. Examples of the PARP inhibitor include compounds having hydroxy group, such as 1H-benzimidazole-4-carboxamide derivatives, olaparib derivatives, rucaparib derivatives, veliparib derivatives, iniparib derivatives, niraparib derivatives, BMN673 (5-Fluoro-8(S)-(4-fluorophenyl)-9 (R)-(1-methyl-1H-1,2,4-triazol-5-yl)-3,7,8,9-tetrahydro-2H-pyrido[4,3,2-de]phthalazin-3-one) derivatives, E7016-related compounds and the like. Among these, the anti-cancer effect enhancer is preferably selected from the group consisting of 1H-benzimidazole-4-carboxamide derivatives, olaparib derivatives, rucaparib derivatives and BMN673 derivatives. A compound which is a substituent of $R_3$ may be a single compound or multiple compounds in a single molecule or among different molecules. Said substituent is preferably the same.

When the anti-cancer effect enhancer has a phenolic hydroxy group in its molecule, said phenolic hydroxy group and a side chain carboxy group of the polyglutamic acid structural moiety of the block copolymer may be bound through an ester bond.

When the anti-cancer effect enhancer has a phenolic hydroxy group or a primary or secondary alcoholic hydroxy group in its molecule, said hydroxy group and a side chain carboxy group of the polyglutamic acid structural moiety of the block copolymer may be bound using the aspartic acid derivative as a linker. That is, the hydroxy group of anti-cancer effect enhancer and the carboxy group of aspartic acid derivative may be ester-bound, then the other carboxy group may be amidated, and an amino group of the obtained compound and a side chain carboxy group of the polyglutamic acid structural moiety of the block copolymer may be bound through an amide bond. Using said aspartic acid derivative as a linker allows for easy non-enzymatic release of anti-cancer effect enhancer.

Examples of the PARP inhibitor bound to the polymeric compound of the invention include the compounds represented by the following formulae (7)-(17).

[Chemical Formula 4]

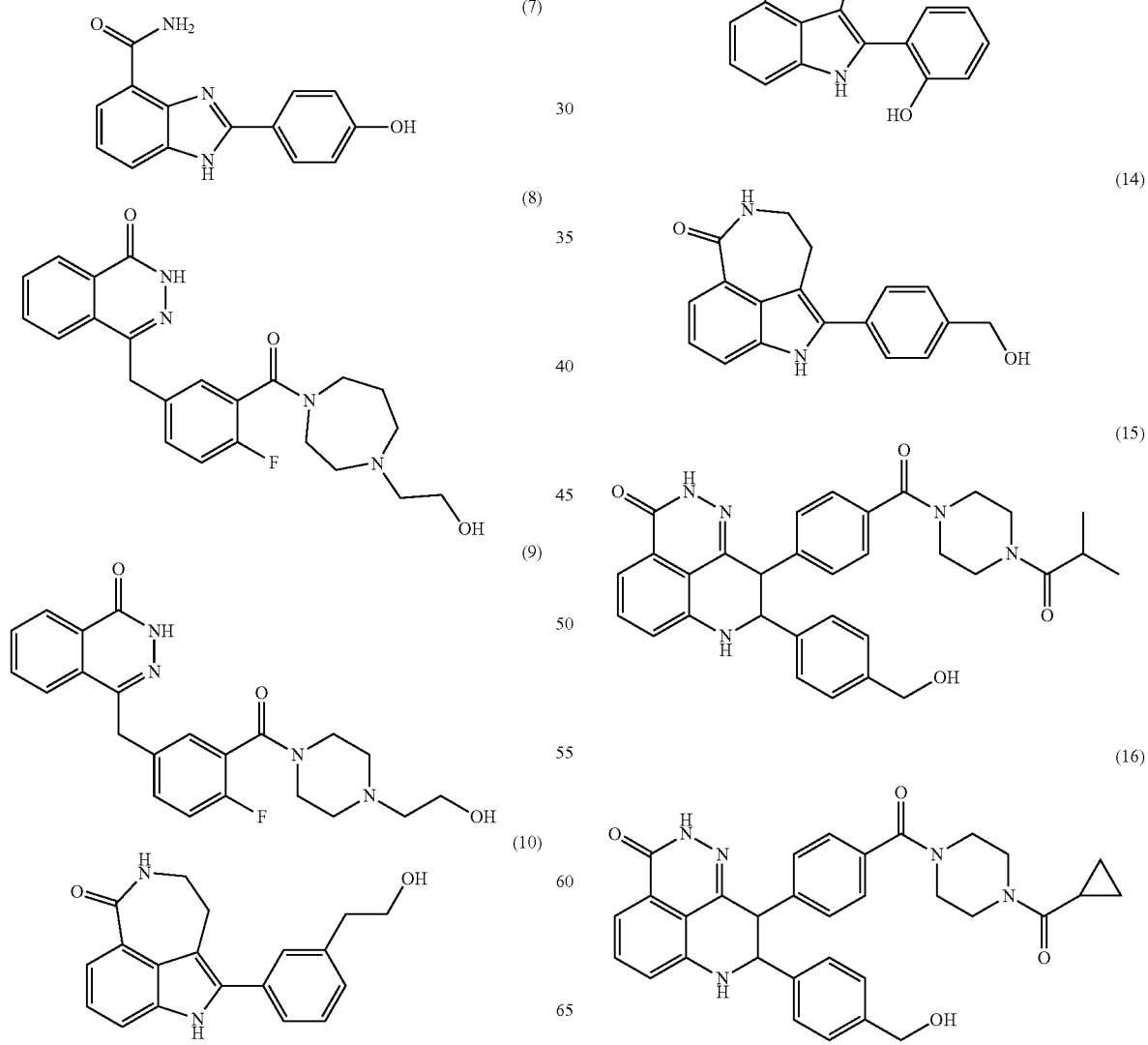

(17)

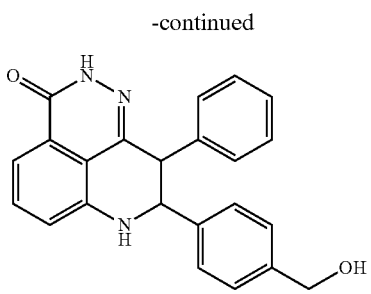

The PARP inhibitors which are directly bound to the block copolymer preferably include 2-(4-hydroxyphenyl)-1H-benzimidazole-4-carboxamide (NU1085) represented by formula (7), 2-(4'-hydroxyphenyl)-3,4,5,6-tetrahydro-1H-azepino[5,4,3-cd]indol-6-one represented by formula (12) and the like. The PARP inhibitors which are bound to the block copolymer using the aspartic acid derivative as a linker preferably include 2-(4'-hydroxymethylphenyl)-3,4,5,6-tetrahydro-1H-azepino[5,4,3-cd]indol-6-one represented by formula (14), 4-[4-fluoro-3-([1,4]diazepane-1-carbonyl-4-hydroxyethyl)benzyl]-2H-phthalazin-1-one represented by formula (8) and the like.

The compound represented by formula (7) is known per se, and it can be prepared, for example, as described in J. Med. Chem., 43, 4084 (2000).

The compounds represented by formulae (8) and (9) are known per se, and they can be prepared, for example, as described in J. Med. Chem., 51, 6581 (2008).

The compounds represented by formulae (10)-(14) are known per se, and they can be prepared, for example, as described in WO 2000/042040.

The compounds represented by formulae (15)-(17) are known per se, and they can be prepared, for example, as described in WO 2010/017055.

The residue of the compound obtained by ester-binding the hydroxy group of anti-cancer effect enhancer to the carboxy group of aspartic acid derivative which is a linker may be, for example, a group represented by said general formula (2) or (3), wherein $R_8$ and $R_9$ each independently represents hydrogen atom or (C1-C6)alkyl group;

$R_{10}$ represents hydrogen atom, (C1-C40)alkyl group which may have a substituent, (C1-C40)aralkyl group which may have a substituent, an aromatic group which may have a substituent, or an amino acid residue having a protected carboxy group;

CX—CY represents CH—CH or C=C (double bond);

OD (O is oxygen atom) represents a residue of anti-cancer effect enhancer. That is, the linker of aspartic acid derivative in the invention includes a group represented by said general formula (2) or (3) wherein CX—CY is C=C (double bond).

When CX—CY is C=C (double bond), the E-configuration is preferable. In addition, HOD represents the anti-cancer effect enhancer.

Examples of the (C1-C6)alkyl group include methyl, ethyl, n-propyl, isopropyl, n-butyl, s-butyl, isobutyl, n-pentyl, n-hexyl groups and the like.

Both $R_8$ and $R_9$ are preferably hydrogen atom.

Examples of the (C1-C40) alkyl group in the (C1-C40) alkyl group which may have a substituent include methyl, ethyl, n-propyl, isopropyl, n-butyl, s-butyl, isobutyl, n-pentyl, n-hexyl, n-stearyl and the like. Examples of the substituent include phenyl, naphthyl, benzyl, methoxy, ethoxy, dimethylamino groups and the like.

Examples of the (C1-C40)aralkyl group in the (C1-C40) aralkyl group which may have a substituent include benzyl, naphtylmethyl, phenethyl, 4-phenylbutyl groups and the like. Examples of the substituent include methyl, ethyl and nitro groups, chlorine and bromine atoms, dimethylamino group, and the like.

Examples of the aromatic group which may have a substituent include groups derived from aniline, nitroaniline, chloroaniline, aminofluorobenzonitrile, aminonaphthalene, aminoflavone, aminofluorene and the like.

The substitution positions of the substituent in each group are not particularly limited as far as it can be substituted thereon. The number of substituent is not specifically limited, either.

As for the amino acid of the amino acid residue having a protected carboxy group, an amino acid having a protected carboxy group that is commonly used for peptide synthesis can be mentioned. A compound in which the carboxy group of the amino acid is protected by ester or amide is preferable. Examples of the compound protected by ester include (C1-C12)alkyl ester of amino acid which may have a substituent, such as (C1-C12)alkyl ester of alanine, .alpha. or .beta. (C1-C12)alkyl ester of aspartic acid, .alpha. or .gamma. (C1-C12)alkyl ester of glutamic acid, (C1-C12)alkyl ester of phenylalanine, (C1-C12)alkyl ester of cysteine, (C1-C12) alkyl ester of glycine, (C1-C12)alkyl ester of leucine, (C1-C12)alkyl ester of isoleucine, (C1-C12)alkyl ester of histidine, (C1-C12)alkyl ester of proline, (C1-C12)alkyl ester of serine, (C1-C12)alkyl ester of threonine, (C1-C12)alkyl ester of valine, (C1-C12)alkyl ester of tryptophan or (C1-C12)alkyl ester of tyrosine. In particular, phenylalanine methyl ester, glycine methyl ester, glycine (4-phenyl-1-butanol)ester, leucine methyl ester, phenylalanine benzyl ester, phenylalanine (4-phenyl-1-butanol)ester are preferable. The amino acid may be D- or L-form, or a mixture thereof.

Examples of the sugar in the sugar residue include glucosamine, galactosamine, and mannosamine, and examples of the substituent include acetyl, pivaloyl, benzyl, and methyl groups. The sugar may be D- or L-form, or a mixture thereof. The number of substituent and the substitution position of the substituent are not particularly limited as long as they are admissible.

In particular, $R_{10}$ is preferably n-butyl, phenylbutyl group or the like. Among these, phenylbutyl group is more preferable.

CX—CY is preferable CH—CH.

$R_4$ in the general formula (1) represents aspartic acid residue and/or aspartic acid imide residue. For example, $R_4$ is preferably selected from the group consisting of substituents represented by said general formulae (4), (5) and (6), wherein $R_8$, $R_9$, and $R_{10}$ and CX—CY have the same meanings as above;

$R_{11}$ represents hydroxy group or $N(R_{12})CONH(R_{12})$; and $R_{12}$ and $R_{13}$, which may be the same or different from each other, represent (C3-C6)branched or cyclic alkyl, or (C1-C5)branched or linear alkyl group which may be substituted with a tertiary amino group. These groups may be together included in the polymeric compound.

$R_8$, $R_9$, $R_{10}$ and CX—CY are the same as the groups $R_8$, $R_9$, $R_{10}$ and CX—CY in said $R_9$, and their preferred groups are also the same.

As well as those of said $R_5$, examples of said (C3-C6) branched or cyclic alkyl group include isopropyl, isobutyl, sec-butyl, tert-butyl, 1-methylbutyl, 2-methylbutyl, neopentyl, cyclohexyl group and the like. Preferably, said (C3-C6)

branched or cyclic alkyl group is isopropyl or cyclohexyl group. Examples of said (C1-C5) branched or linear alkyl group which may be substituted by a tertiary amino group include ethyl, dimethylaminopropyl groups and the like.

The polyglutamic acid structural moiety in the general formula (1) may have a glutamic acid moiety. In the general formula (1), the glutamic acid moiety is in the form of free acid, but may be in the form of alkali metal salt or alkaline-earth metal salt, included in the invention. Examples of the alkali metal salt or the alkaline-earth metal salt include lithium salt, sodium salt, potassium salt, magnesium salt, calcium salt and the like. When the polymeric compound is parenterally administered as an anti-cancer agent, its solution is prepared by using a liquid dissolving it. The salt of glutamic acid may be based on its salt with cation of pH buffer of said solution.

The polyglutamic acid structural moiety in the invention comprises a glutamic acid unit (the number of unit is d) having a camptothecin derivative (EHC) bound to a side chain carboxy group, and a glutamic acid unit (the number of unit is e) having said $R_3$ bound to a side chain carboxy group, as well as a glutamic acid unit (the number of unit is f) having said $R_4$ bound to a side chain carboxy group, a glutamic acid unit (the number of unit is g) having said $R_5$ bound to a side chain carboxy group, and a glutamic acid unit (the number of unit is h) in which a side chain carboxy group is in the form of free carboxy group or its salt. Each unit may be independently and randomly arranged.

The total amount of glutamic acid units in the polyglutamic acid structural moiety of the block copolymer represented by the general formula (1) is represented by the formula d+e+f+g+h. The ratio of d is 5-50%, preferably 5-40%; the ratio of e is 5-90%, preferably 5-80%; the ratio of f is 0-90%, preferably 0-60%; the ratio of g is 0-90%, preferably 5-40%; and the ratio of h is 0-90%, preferably 0-30%.

The polymeric compound of the invention may form in water a micelle having a polyethylene glycol structural moiety as the outer shell and a polyglutamic acid structural moiety to which drugs are bound as the inner shell.

Then, a method for producing the polymeric compound of the invention will be illustrated below. However, the method for producing the polymeric compound of the invention is not limited to the methods as described hereinafter, and in Examples and Reference Examples.

A method of generating a main chain of the block copolymer having a polyethylene glycol structural moiety and a polyglutamic acid structural moiety, which is the polymeric compound of the invention represented by the general formula (1) may be either of the following methods: a method of linking a polyethylene glycol structural moiety to a polyglutamic acid structural moiety; and a method of polymerizing glutamic acid to a polyethylene glycol structural moiety through sequentially polymerization.

As an example of the latter method, based on a method as described in WO 2006/120914 etc., N-carbonyl glutamic acid anhydride is sequentially reacted with the modified polyethylene glycol in which the single end is modified with methyl and the other single end is modified with aminopropyl group. In this case, N-carbonyl glutamic acid anhydride is preferably a compound in which the carboxy group of glutamic acid side chain is modified with an appropriate carboxylic acid protecting group. Said carboxylic acid protecting group is not limited to, but preferably an ester-type protecting group, particularly preferably benzyl ester. After the reaction, the obtained compound is deprotected through the alkaline hydrolysis or hydrogenolysis reaction to form the desired block copolymer.

Before the deprotection, a terminal amino group of the polyglutamic acid structural moiety of the block copolymer may be acylated.

Hereinafter, a method for binding a drug etc. to a side chain in the polymeric compound represented by the general formula (1) will be illustrated.

EHC, and an anti-cancer effect enhancer or an aspartic acid derivative to which an anti-cancer effect enhancer are bound to the above block copolymer having a polyethylene glycol structural moiety and a polyglutamic acid structural moiety. The method of binding includes, but not limited to, the following: EHC may be first bonded, and then the anti-cancer effect enhancer or the aspartic acid derivative to which the anti-cancer effect enhancer is bound may be bonded, or they may be bonded in the reverse order of this, or they may be simultaneously bonded. An example of method for producing an aspartic acid derivative to which an anti-cancer effect enhancer is bound will be described below.

Preferably, the block copolymer having a polyethylene glycol structural moiety and a polyglutamic acid structural moiety, EHC, and an anti-cancer effect enhancer or an aspartic acid derivative to which an anti-cancer effect enhancer is bound may be reacted via dehydration condensation in the presence of a carbodiimide dehydration-condensation agent. According to this method, the group $N(R_6)CONH(R_7)$ can be also introduced into the block copolymer simultaneously. Examples of the carbodiimide dehydration-condensation agent include dicyclohexylcarbodiimide (DCC), diisopropylcarbodiimide (DIPCI), 1-ethyl-3-(3-dimethylaminopropyl)carbodiimide hydrochloride (WSC) and the like. In the dehydration condensation reaction, a reaction aid such as N,N-dimethylaminopyridine (DMAP) or the like may be used. When an aspartic acid derivative to which an anti-cancer effect enhancer is bound is bonded, the group $N(R_{12})CONH(R_{13})$ may be optionally introduced to $R_{11}$.

The polymeric compound of the invention can be produced via an optional purification process after the above reaction.

The polymeric compound of the invention gradually dissociates and releases antitumor active ingredients, i.e. EHC and an anti-cancer effect enhancer in phosphate buffered physiological saline (PBS) solution. This indicates that the compound has a property of sustained release of the EHC and the anti-cancer effect enhancer in the administration of said compound. Moreover, the ratio of the EHC and the anti-cancer effect enhancer to be bound can be changed appropriately. The dose of them can be also changed appropriately.

It is known that the pharmacokinetics and the body distribution of a high molecular compound are significantly different from those of a low molecular compound. In light of this, the polymeric compound of the invention exhibits the different efficacy and the different side effect from those of a low molecular compound drug. Accordingly, a new treatment method using a camptothecin derivative and an anti-cancer effect enhancer can be provided.

The polymeric compound of the invention can be used as an anticancer agent. Said use is also included in the invention. Said anticancer agent may be used in a conventionally used formulation such as injections, drops, tablets, capsules and powders. For formulation process, pharmaceutically acceptable carriers or additives which are conventionally used, can be used. Examples of said carriers or additives include binding agents, lubricating agents, disintegrating agents, solvents, vehicles, solubilizing agents, dispersing agents, stabilizing agents, suspending agents, preservatives, soothing agents, colorants, flavors and the like. Said anticancer agent is preferably used as injections or drops. In particular, water, physiological saline, 5% glucose or mannitol solution, water-soluble organic solvent (for example, glycerol, ethanol, dimethylsulfoxide, N-methylpyrolidone, polyethylene glycol, cremophor and the like, and mixtures thereof), and mixtures of water and the water-soluble organic solvents are preferably used.

The dosage of the polymeric compound may vary as a matter of course, depending on the sex, age, body constitution, physiological condition, pathological condition and the like of a patient. For example, the polymeric compound is parenterally administered at a dose as an active ingredient, EHC, of 0.01-500 mg/m$^2$, preferably 1-200 mg/m$^2$ body surface area of patient per day for an adult.

The polymeric compound of the invention can enhance the therapeutic effect of camptothecin derivative. Said polymeric compound can be applied to a breast cancer, ovarian cancer, lung cancer, thyroid cancer, myeloid leukemia, hepatoblastoma, colon cancer, gallbladder cancer or the like. In particular, said polymeric compound can be expected to have a high therapeutic effect in the chemotherapy of various cancers pre-treated by a camptothecin derivative.

EXAMPLES

Hereinafter, the invention will be illustrated more specifically with reference to Examples. However, the scope of the invention is not limited to these Examples. The Gaussian distribution analysis for measuring the size of the particles (i.e. particle diameter) that are constituted by the product of invention in an aqueous solution was conducted by using a ZetaPotential/Particlesizer NICOMP™ 380ZLS (manufactured by Particle Sizing Systems Co.).

Example 1

Polymeric compound having EHC and 2-(4-hydroxyphenyl)-1H-benzimidazole-4-carboxamide (NU1085) bound thereto (Compound 1:$R_1$=Me, $R_2$=acetyl group, A=trimethylene group, $R_6$=$R_7$=isopropyl group, d+e+f+g+h=23, t=273)

462 mg of methoxy polyethylene glycol-polyglutamic acid block copolymer (the block copolymer comprising the methoxy polyethylene glycol structural moiety having the molecular weight of 12,000 and having methyl group at the single end and aminopropyl group at the other end, and the polyglutamic acid structural moiety (having the terminal N-acetyl group) having the polymerization number of 23, and having the linking group which is trimethylene group), which was prepared according to the method described in WO 2006/120914, 70 mg of EHC and 70 mg of 2-(4-hydroxyphenyl)-1H-benzimidazole-4-carboxamide (NU1085; the compound represented by formula (7)) were dissolved in 8.5 ml of DMF, stirred at 35° C. for 15 minutes, and then stirred at 20° C. for 1 hour. Subsequently, 204 µl of DIPCI and 8.0 mg of DMAP were added to the solution, and stirred at 20° C. for 21 hours. 102 µl of DIPCI was added to the solution, and further stirred for 4 hours. The reaction solution was slowly dropped into the mixture solution of 8.5 ml of ethanol, 8.5 ml of ethyl acetate and 68 ml of diisopropylether, and stirred at room temperature for 1 hour. The obtained precipitates were filtered, and washed with ethanol/diisopropylether (1/4 (v/v)). The obtained precipitates were dissolved in 35 ml of acetonitrile and 3.5 ml of water, then added with ion exchange resin (trade name: DOWEX 50(H+), manufactured by Dow Chemical Company, 7.0 ml), stirred and filtered. Acetonitrile in the obtained filtrate was distilled off under reduced pressure, and then the filtrate was freeze dried to yield Compound 1 (530 mg).

1N-aqueous sodium hydroxide solution was added to Compound 1, and stirred at 37° C. for 1 hour. The released EHC and NU1085 were analyzed by HPLC (high performance liquid chromatography), and the contents of EHC and NU1085 bound to Compound 1 were calculated from the amounts of EHC and NU1085 obtained from the calibration curve established with EHC and NU1085. As a result, the contents of the bound EHC and NU1085 were 10.4% (w/w) and 10.2% (w/w), respectively.

Gaussian distribution analysis was carried out for the aqueous solution (1 mg/ml) of Compound 1. As a result, it was found to be 16 nm (volume weighting). Thus, it was believed that Compound 1 formed a micelle in water.

Example 2

Polymeric compound having EHC and 2-(4'-hydroxyphenyl)-3,4,5,6-tetrahydro-1H-azepino[5,4,3-cd]indol-6-one (PARP inhibitor 2) bound thereto (Compound 2)

453 mg of methoxy polyethylene glycol-polyglutamic acid block copolymer as described in Example 1, which was prepared according to the method described in WO 2006/120914, 60 mg of EHC and 60 mg of 2-(4'-hydroxyphenyl)-3,4,5,6-tetrahydro-1H-azepino[5,4,3-cd]indol-6-one (PARP inhibitor 2; the compound represented by formula (12)) were dissolved in 8.4 ml of DMF, stirred at 35° C. for 25 minutes, and then stirred at 20° C. for 1 hour. 225 µl of DIPCI and 8.2 mg of DMAP were added to the solution, and stirred at 20° C. for 22.5 hours. 49 µl of DIPCI was added to the solution, and further stirred for 3.25 hours. The reaction solution was slowly dropped into the mixture solution of ml of ethanol, 3 ml of ethyl acetate and 80 ml of diisopropylether, and stirred at room temperature for 1 hour. The obtained precipitates were filtered, and washed with ethanol/diisopropylether (1/4 (v/v)). The obtained precipitates were dissolved in 37 ml of acetonitrile and 3.7 ml of water, then added with ion exchange resin (trade name: DOWEX 50(H+), manufactured by Dow Chemical Company, 3.7 ml), stirred and filtered. Acetonitrile in the obtained filtrate was distilled off under reduced pressure, and then the filtrate was freeze dried to yield Compound 2 (513 mg).

1N-aqueous sodium hydroxide solution was added to Compound 2, and stirred at 37° C. for 1 hour. The released EHC and PARP inhibitor 2 were analyzed by HPLC (high performance liquid chromatography), and the contents of EHC and PARP inhibitor 2 bound to Compound 2 were calculated from the amounts of EHC and PARP inhibitor 2 obtained from the calibration curve established with EHC and PARP inhibitor 2. As a result, The contents of the bound EHC and PARP inhibitor 2 were 10.8% (w/w) and 9.6% (w/w), respectively.

Gaussian distribution analysis was carried out for the aqueous solution (1 mg/ml) of Compound 2. As a result, it was found to be 29 nm (volume weighting). Thus, it was believed that Compound 2 formed a micelle in water.

Synthetic Example 1

Synthesis of N-(tert-butoxycarbonyl)aspartic acid-1-phenylbutylamide-4-benzyl ester (Compound 3)

5.0 g of N-(tert-butoxycarbonyl)aspartic acid-4-benzyl ester and 2.4 ml of 1-phenylbutylamine were dissolved in 30 ml of DMF, added with 3.8 g of WSC hydrochloride salt and 2.2 g of HOBt (N-hydroxybenzotriazole), and then stirred for 5 hours at room temperature. Water was added to the reaction solution, extracted with ethyl acetate, and washed with saturated aqueous solution of sodium hydrogen carbonate. After drying of the solution with magnesium sulfate, ethyl acetate was distilled off under reduced pressure followed by vacuum drying to yield 7.2 g of Compound 3.

MS: m/z 477 (M+Na)$^+$, the calculated value as $C_{26}H_{34}N_2O_5$: 477 (M+Na)$^+$ Synthetic Example 2

Synthesis of N-(tert-butoxycarbonyl)aspartic acid-1-phenyl butylamide (Compound 4)

7.2 g of Compound 3 obtained in Synthetic example 1 was dissolved in 30 ml of ethyl acetate, added with 2.8 g of 5% palladium carbon (water content: 50%). Then, the atmosphere in the system was replaced with hydrogen, and the solution was stirred overnight at room temperature under hydrogen atmosphere. 5% palladium carbon was filtered, washed with ethyl acetate, and then the filtrate and the wash solution was combined. Ethyl acetate was distilled off under reduced pressure followed by vacuum drying to yield 5.4 g of Compound 4.

MS: m/z 387 (M+Na)$^+$, the calculated value as $C_{19}H_{28}N_2O_5$: 387 (M+Na)$^+$ Synthetic Example 3

Synthesis of the Ester Compound of N-(tert-butoxycarbonyl)aspartic acid-1-phenylbutylamide with 2-(4'-hydroxymethylphenyl)-3,4,5,6-tetrahydro-1H-azepino[5,4,3-cd]indol-6-one (Compound 5)

1.11 g of Compound 4 obtained in Synthetic example 2 and 745 mg of 2-(4'-hydroxymethylphenyl)-3,4,5,6-tetrahydro-1H-azepino[5,4,3-cd]indol-6-one (PARP inhibitor 3; the compound represented by formula (14)) were dissolved in 13 ml of DMF, added with 743 µl of DIPCI and 31 mg of DMAP, and then stirred for 18 hours at room temperature. Water was added to the reaction solution, extracted with ethyl acetate, and washed with saturated aqueous solution of sodium hydrogen carbonate and saturated aqueous solution of sodium chloride in order. After drying the solution with sodium sulfate, ethyl acetate was distilled off under reduced pressure. The obtained oily matter was purified with silica-gel chromatography (CHCl$_3$/MeOH) to yield 2.12 g of Compound 5.

MS: m/z 639 (M+H)$^+$, the calculated value as $C_{37}H_{43}N_4O_6$: 639 (M+H)$^+$ Synthetic Example 4

Synthesis of the Ester Compound of Aspartic Acid-1-phenylbutylamide with PARP Inhibitor 3 (Compound 6)

To 2.06 g of Compound 5 obtained in Synthetic example 3, 20 ml of 4N-HCl ethyl acetate solution was added and stirred for 3 hours at room temperature. After the reaction, ethyl acetate was distilled off under the reduced pressure to yield 2.36 g of Compound 6.

MS: m/z 539 (M+H)$^+$, the calculated value as $C_{32}H_{35}N_4O_4$: 539 (M+H)$^+$ Example 3

Synthesis of Polymeric Compound Having EHC and Compound 6 Bound Thereto (Compound 7: $R_1$=Me, $R_2$=acetyl group, A=trimethylene group, $R_8$=$R_9$=hydrogen atom, $R_{10}$=1-phenylbutyl group, $R_6$=$R_7$=$R_{12}$=$R_{13}$=isopropyl group, $R_{11}$=hydroxy group, d+e+f+g+h=23, t=273)

403 mg of methoxy polyethylene glycol-polyglutamic acid block copolymer as described in Example 1, which was prepared according to the method described in WO 2006/120914, was dissolved in 7.5 ml of DMF, stirred at 35° C. for 30 minutes, and then stirred at 25° C. for 1 hour. Subsequently, 60 mg of EHC and 44 µl of DIPCI and 7.3 mg of DMAP were added to the solution, and stirred at 25° C. for 4.5 hours. 190 mg of Compound 6 obtained in Synthetic example 4, 63 µl of N,N-diisopropylethylamine and 130 µl of DIPCI were added to the solution, and further stirred for 18.5 hours. The reaction solution was slowly dropped into the mixture solution of 15 ml of ethanol, 15 ml of ethyl acetate and 120 ml of diisopropylether, and stirred at room temperature for 1 hour. The obtained precipitates were filtered, and washed with ethanol/diisopropylether (1/4 (v/v)). The obtained precipitates were dissolved in 38 ml of acetonitrile and 3.8 ml of water, then added with ion exchange resin (trade name: DOWEX 50(H+), manufactured by Dow Chemical Company, 7.6 ml), stirred and filtered. Acetonitrile in the obtained filtrate was distilled off under reduced pressure, and then the filtrate was freeze dried to yield 510 mg of Compound 7.

1N-aqueous sodium hydroxide solution was added to Compound 7, and stirred at 37° C. for 1 hour. The released EHC and PARP inhibitor 3 were analyzed by HPLC (high performance liquid chromatography), and the contents of EHC and PARP inhibitor 3 bound to Compound 7 were calculated from the amounts of EHC and PARP inhibitor 3 obtained from the calibration curve established with EHC and PARP inhibitor 3. As a result, the contents of the bound EHC and PARP inhibitor 3 were 12.0% (w/w) and 7.1% (w/w), respectively.

Gaussian distribution analysis was carried out for the aqueous solution (1 mg/ml) of Compound 7. As a result, it was found to be 22 nm (volume weighting). Thus, it was believed that Compound 7 formed a micelle in water.

Synthetic Example 5

Synthesis of the Ester Compound of N-(tert-butoxycarbonyl)aspartic acid-1-phenylbutylamide with 4-[4-fluoro-3-([1,4]diazepane-1-carbonyl-4-hydroxyethyl)benzyl]-2H-phthalazin-1-one (Compound 8)

1.5 g of Compound 4 obtained in Synthetic example 2 and 2.1 g of 4-[4-fluoro-3-([1,4]diazepane-1-carbonyl-4-hydroxyethyl)benzyl]-2H-phthalazin-1-one (PARP inhibitor 4: the compound represented by formula (8)) were dissolved in 8.2 ml of DMF, added with 1.3 ml of DIPCI and 50 mg of DMAP, stirred at room temperature for 20 hours. Water was added to the reaction solution, extracted with ethyl acetate, washed with saturated aqueous solution of sodium hydrogen carbonate and saturated aqueous solution of sodium chloride in order. After drying the solution with magnesium sulfate, ethyl acetate was distilled off under reduced pressure. The obtained oily matter was purified with silica-gel chromatography (CHCl.sub.3/MeOH) to yield 2.6 g of Compound 8.

MS: m/z 771 (M+H)$^+$, the calculated value as C$_{42}$H$_{51}$FN$_6$O$_7$: 771 (M+H)$^+$ Synthetic Example 6

Synthesis of the ester compound of aspartic acid-1-phenylbutylamide with PARP Inhibitor 4 (Compound 9)

1.6 g of Compound 8 obtained in Synthetic example 5 was dissolved in 5.1 ml of ethyl acetate, added with 5.1 ml of 4N-HCl ethyl acetate solution, and then stirred at room temperature for 1 hour. After the reaction, ethyl acetate was distilled off under the reduced pressure to yield 1.4 g of Compound 9.

MS: m/z 671 (M+H)$^+$, the calculated value as C$_{38}$H$_{45}$FN$_6$O$_5$: 671 (M+H)$^+$ Example 4 Polymeric Compound Having EHC and Compound 9 Bound Thereto (Compound 10)

518 mg of methoxy polyethylene glycol-polyglutamic acid block copolymer as described in Example 1, which was prepared according to the method described in WO 2006/120914, was dissolved in 8.0 ml of DMF, stirred at 35° C. for 15 minutes, and then stirred at 25° C. for 1 hour. Subsequently, 100 mg of EHC and 60 μl of DIPCI and 9.4 mg of DMAP were added to the obtained solution, and then stirred at 25° C. for 6 hours. 149 mg of Compound 9 obtained in Synthetic example 6, 38 μl of N,N-diisopropylethylamine and 180 μl of DIPCI were added to the solution, and further stirred for 18 hours. The reaction solution was slowly dropped into the mixture solution of 10 ml of ethanol, 10 ml of ethyl acetate and 80 ml of diisopropylether, and stirred at room temperature for 1 hour. The precipitates were filtered and washed with ethanol/diisopropylether (1/4 (v/v)). The obtained precipitates were dissolved in 40 ml of acetonitrile and 4.0 ml of water, added with ion exchange resin (trade name: DOWEX 50(H+), manufactured by Dow Chemical Company, 8.0 ml), stirred and filtered. Acetonitrile in the obtained filtrate was distilled off under reduced pressure, and then freeze dried to yield 650 mg of Compound 10.

1N-aqueous sodium hydroxide solution was added to Compound 10, and stirred at 37° C. for 1 hour. The released EHC and PARP inhibitor 4 were analyzed by HPLC (high performance liquid chromatography), and the contents of EHC and PARP inhibitor 4 bound to Compound 10 were calculated from the amounts of EHC and PARP inhibitor 4 obtained from the calibration curve established with EHC and PARP inhibitor 4. As a result, the contents of the bound EHC and PARP inhibitor 4 were 11.3% (w/w) and 15.6% (w/w), respectively.

Gaussian distribution analysis was carried out for the aqueous solution (1 mg/ml) of Compound 10. As a result, it was found to be 22 nm (volume weighting). Thus, it was believed that Compound 10 formed a micelle in water.

Reference Example 1

Polymeric compound having 2-(4'-hydroxyphenyl)-1H-benzimidazole-4-carboxamide (NU1085) Bound Thereto (Compound 11: Control Drug 2)

1.97 g of methoxy polyethylene glycol-polyglutamic acid block copolymer as described in Example 1, which was prepared according to the method described in WO 2006/120914, and 400 mg of NU1085 were dissolved in 35 ml of DMF, stirred at 35° C. for 20 minutes, and then stirred at 20° C. for 1 hour. 856 μl of DIPCI and 35 mg of DMAP were added to the solution, and stirred at 20° C. for 19 hours. 102 μl of DIPCI was added to the solution, and further stirred for 3 hours. The reaction solution was slowly dropped into the mixture solution of 35 ml of ethanol, 35 ml of ethyl acetate and 280 ml of diisopropylether, and stirred at room temperature for 2 hours. The obtained precipitates were filtered, and washed with ethanol/diisopropylether (1/4 (v/v)). The obtained precipitates were dissolved in 40 ml of acetonitrile and 4 ml of water, then added with ion exchange resin (trade name: DOWEX 50(H+), manufactured by Dow Chemical Company, 12 ml), stirred and filtered. Acetonitrile in the obtained filtrate was distilled off under reduced pressure, and then the filtrate was freeze dried to yield 1.96 g of Compound 11.

1N-aqueous sodium hydroxide solution was added to Compound 11, and stirred at 37° C. for 1 hour. The released NU1085 were analyzed by HPLC (high performance liquid chromatography), and the content of NU1085 bound to Compound 11 was calculated from the amounts of NU1085 obtained from the calibration curve established with NU1085. As a result, the content of the bound NU1085 was 14.6% (w/w).

Gaussian distribution analysis was carried out for the aqueous solution (1 mg/ml) of Compound 11. As a result, it was found to be 18 nm (volume weighting). Thus, it was believed that Compound 11 formed a micelle in water.

Example 5

Polymeric Compound Having EHC and 2-(4-hydroxyphenyl)-1H-benzimidazole-4-carboxamide (NU1085) Bound Thereto (Compound 12: R$_1$=Me, R$_2$=Acetyl Group, A=Propylene Group, R$_6$=R$_7$=Isopropyl Group, d+e+f+g+h=10, t=114)

620 mg of methoxy polyethylene glycol-polyglutamic acid block copolymer (the block copolymer comprising the polyethylene glycol structural moiety having molecular weight of 5,000 and having methyl group at the single end and aminopropyl group at the other end, and the polyglutamic acid structural moiety (having the terminal N-acetyl group) having the polymerization number of 10), which was prepared according to the method described in WO 2006/120914, 100 mg of EHC and 100 mg of 2-(4-hydroxyphenyl)benzimidazole-1H-4-carboxamide (NU1085) were dissolved in 12 ml of DMF, stirred at 35° C. for 35 minutes, and stirred at 20° C. for 1 hour. Subsequently, 307 μl of DIPCI and 12 mg of DMAP were added to the solution, and stirred at 20° C. for 18 hours. 154 μl of DIPCI was added to the solution, further stirred for 4 hours. The reaction solution was slowly dropped into the mixture solution of 36 ml of ethyl acetate and 144 ml of diisopropylether and stirred at room temperature for 1 hour. The obtained precipitates were filtered, and washed with ethyl acetate. The obtained precipitates were dissolved in 8.0 ml of acetonitrile and 2.0 ml of water, then added with ion exchange resin (trade name: DOWEX 50(H+), manufactured by Dow Chemical Company, 4.0 ml), stirred and filtered. Acetonitrile in the obtained filtrate was distilled off under reduced pressure, and then the filtrate was freeze dried to yield Compound 12 (750 mg).

1N-aqueous sodium hydroxide solution was added to Compound 12, and stirred at 37° C. for 1 hour. The released EHC and NU1085 were analyzed by HPLC (high performance liquid chromatography), and the contents of EHC and NU1085 bound to Compound 12 were calculated from the amounts of EHC and NU1085 obtained from the calibration curve established with EHC and NU1085. As a result, the contents of the bound EHC and NU1085 were 10.5% (w/w) and 12.0% (w/w), respectively.

Gaussian distribution analysis was carried out for the aqueous solution (1 mg/ml) of Compound 12. As a result, it was found to be 6 nm (volume weighting). Thus, it was believed that Compound 12 formed a micelle in water.

Example 6 Polymeric Compound Having EHC and Compound 9 Bound Thereto (Compound 13)

164 mg of methoxy polyethylene glycol-polyglutamic acid block copolymer (the block copolymer comprising the polyethylene glycol structural moiety having the molecular weight of 5,000 and having methyl group at the single end and aminopropyl group at the other end, and the polyglutamic acid structural moiety (having the terminal N-acetyl group) having the polymerization number of 10), which was prepared according to WO 2006/120914, was dissolved in 5.0 ml of DMF, stirred at 35° C. for 15 minutes, and then stirred at 25° C. for 1 hour. Subsequently, 34 mg of EHC and 20 µl of DIPCI and 3.2 mg of DMAP were added to the solution, and stirred at 25° C. for 6 hours. 50 mg of Compound 9 obtained in Synthetic example 6, 14.6 µl of N,N-diisopropylethylamine and 61 µl of DIPCI were added to the solution, and further stirred for hours. The reaction solution was slowly dropped into the mixture solution of 15 ml of ethyl acetate and 60 ml of diisopropylether, and stirred at room temperature for 3 hours. The obtained precipitates were filtered, and washed with ethyl acetate. The obtained precipitates were dissolved in 8.0 ml of acetonitrile and 2.0 ml of water, then added with ion exchange resin (trade name: DOWEX 50(H+), manufactured by Dow Chemical Company, 2.0 ml), and stirred and filtered. Acetonitrile in the obtained filtrate was distilled off under reduced pressure, and then the filtrate was freeze dried to yield 220 mg of Compound 13.

1N-aqueous sodium hydroxide solution was added to Compound 13, and stirred at 37° C. for 1 hour. The released EHC and PARP inhibitor 4 were analyzed by HPLC (high performance liquid chromatography), and the contents of EHC and PARP inhibitor 4 bound to Compound 13 were calculated from the amounts of EHC and PARP inhibitor 4 obtained from the calibration curve established with EHC and PARP inhibitor 4. As a result, the contents of the bound EHC and PARP inhibitor 4 were 13.3% (w/w) and 11.8% (w/w), respectively.

Gaussian distribution analysis was carried out for the aqueous solution (1 mg/ml) of Compound 13. As a result, it was found to be 18 nm (volume weighting). Thus, it was believed that Compound 13 formed a micelle in water.

Test Example 1

Release of EHC and PARP Inhibitor in the Absence of Enzymes

Compounds 1, 2, 7, 10, 12 and 13 were each dissolved in a concentration of 1 mg/ml in PBS (phosphate buffered physiological saline, pH 7.1), and incubated at 37° C. EHC and PARP inhibitor released from the polymeric compound was analyzed and quantified by HPLC in comparison with a calibration curve. The ratio of the quantified amount to the total amount of the drug determined from the content of the drug in the polymeric compound is shown in FIGS. 1-6.

As seen from FIGS. 1, 2, 3, 4, 5 and 6, the polymeric compounds of the invention (Compounds 1, 2, 7, 10, 12 and 13) simultaneously released EHC and PARP inhibitor in absence of hydrolyzing enzymes. Compounds 1, 2, 7, 10, 12 and 13 released the drugs at nearly the same rate. The release rate of EHC and PARP inhibitor can vary according to types of the bound PARP inhibitor.

Test Example 2

Anti-Tumor Activity Test for EHC and PARP Inhibitor

BRCA1-defective human breast cancer MX-1, maintained by serial subcutaneous subculture in mice, was minced into about 2-mm cubic fragments, and the fragments were subcutaneously transplanted on the dorsal part of nude mice with a trocar. From 18 days after the tumor transplantation, the polymeric compound of the invention (Compound 1), Control Drug 1 (EHC-bound polyethylene glycol-polyglutamic acid block copolymer prepared according to the method described in WO 2006/120914) and Control Drug 1+Control Drug 2 (Compound 11 of Reference Example 1) were each intravenously administered three times every seven days in the dose shown in Table 1. Each compound was dissolved in a 5% aqueous glucose solution or physiological saline and used.

TABLE 1

| Agent | Dose (as EHC) mg/kg |
| --- | --- |
| Untreated | 0 |
| Compound 1 | 1.88 |
| Control drug 1 | 1.88 |
| Control drug 1 + Control drug 2 | 1.88 |

Figure 7:
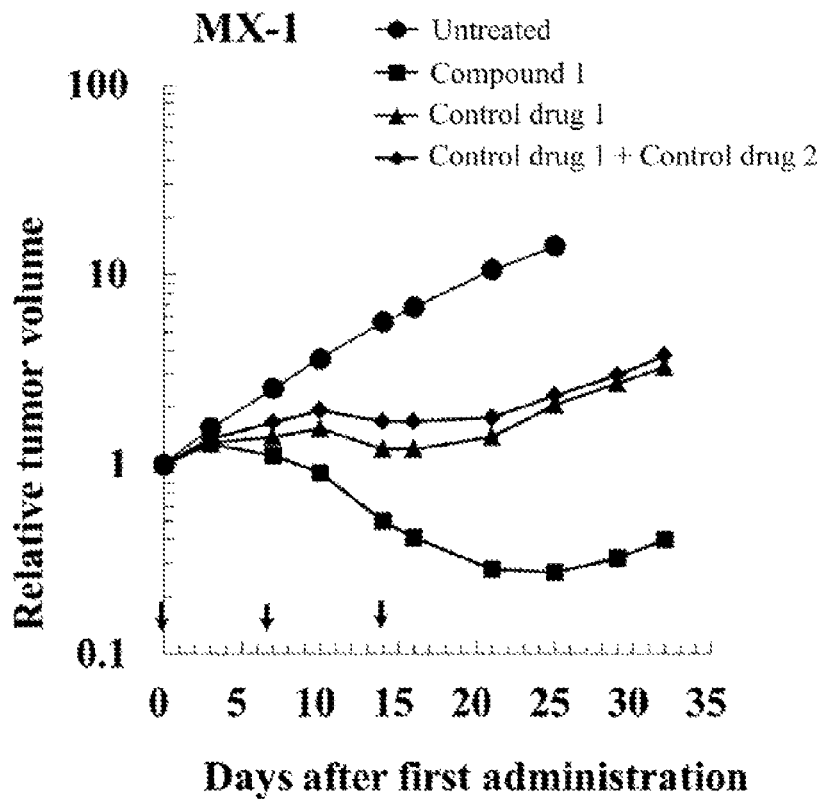
FIG. 7 illustrates the relative tumor volume and its change based on the tumor volume on the start date of administration in each administration group. BRCA1-defective human breast cancer MX-1, maintained by serial subcutaneous subculture in mice, was subcutaneously transplanted on the dorsal part of nude mice. From 18 days after the tumor transplantation, the polymer derivative of the invention (Compound 1), Control Drug 1 or Control Drug 1+Control Drug 2 was administered to the mice.

The major axis (L mm) and the minor axis (W mm) of the tumor were measured over time using a caliper, and the tumor volume on the start date of administration and after the start of administration was calculated by the formula $(L \times W^2)/2$. FIG. 7 shows the change of the relative tumor volume based on the tumor volume on the start date of administration in each administration group.

The results shown in FIG. 7 indicate that Compound 1 of the polymeric compound of the invention has a stronger anti-tumor effect compared in the same dose to Control Drug 1 of the polymeric compound having only EHC, and the combination of Control Drug 1 with Control Drug 2 of the polymeric compound having only PARP inhibitor.

Test Example 3

Anti-Tumor Activity Test for EHC and PARP Inhibitor

Human pancreas cancer BxPC-3, maintained by serial subcutaneous subculture in mice, was minced into about 2-mm cubic fragments, and the fragments were subcutaneously transplanted on the dorsal part of nude mice with a trocar. From 26 days after the tumor transplantation, the polymeric derivatives of the invention (Compounds 1 and 13) and Control Drug 1 (EHC-bound polyethylene glycol-polyglutamic acid block copolymer prepared according to the method described in WO 2006/120914) were each intravenously administered once in the dose shown in Table 2. Each compound was dissolved in a 5% aqueous glucose solution or physiological saline and used.

TABLE 2

| Agent | Dose (as EHC) (mg/kg) |
|---|---|
| Untreated | 0 |
| Compound 1 | 10 |
| Compound 13 | 10 |
| Control drug 1 | 10 |

Figure 8:
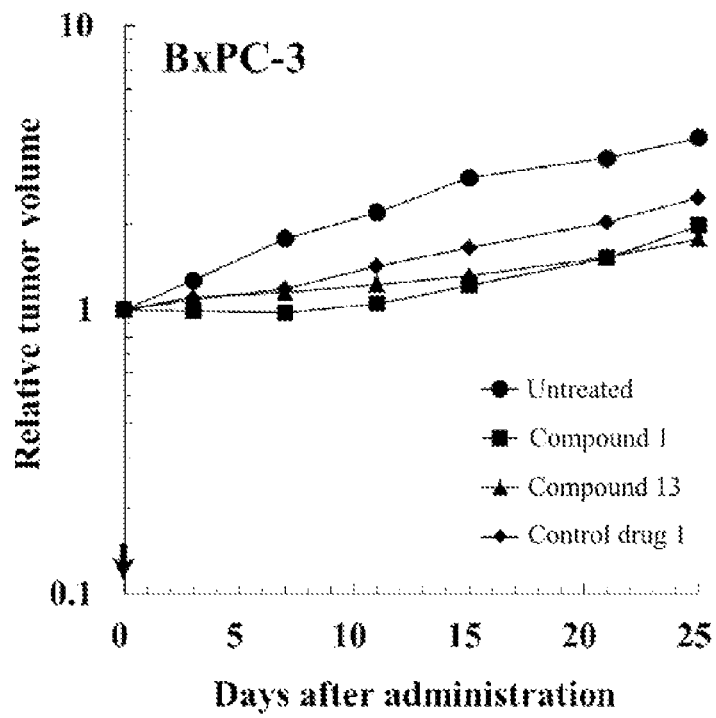
FIG. 8 illustrates the relative tumor volume and its change based on the tumor volume on the start date of administration in each administration group. Human pancreas cancer, BxPC-3, maintained by serial subcutaneous subculture in mice, was subcutaneously transplanted on the dorsal part of nude mice. From 18 days after the tumor transplantation, the polymer derivative of the invention (Compound 1 or 13) or Control Drug 1 was intravenously administered once in the dose shown in Table 2 below.

The major axis (L mm) and the minor axis (W mm) of the tumor were measured over time using a caliper, and the tumor volume on the start date of administration and after the start of administration was calculated by the formula $(L \times W^2)/2$. FIG. 8 shows the relative tumor volume based on the tumor volume on the start date of administration in each administration group.

As seen from the results shown in FIG. 8, Compounds 1 and 13 according to the invention have a stronger anti-tumor effect compared in the same dose to Control Drug 1 of the polymeric compound having only EHC.

The invention claimed is:

1. A polymeric compound represented by the following general formula (1):

(1)

wherein
R₁ represents (C1-C4) alkyl group;
t represents an integer of 45-450;
A represents (C1-C6)alkylene group;
d+e+f+g+h represents an integer of 6-60;
the ratio of d compared to d+e+f+g+h is 5-50%:
the ratio of e compared to d+e+f+g+h is 5-90%;
the ratio of f compared to d+e+f+g+h is 0-90%,
the ratio of g compared to d+e+f+g+h is 0-90%;
the ratio of h compared to d+e+f+g+h is 0-90%;
R₂ represents hydrogen atom or (C1-C4)acyl group;
R₃ represents a residue of a PARP inhibitor having a phenolic hydroxy group or an alcoholic hydroxy group, or an aspartic acid residue to which a PARP inhibitor having a phenolic hydroxy group or an alcoholic hydroxy group is bound, wherein the PARP inhibitor is selected from a compound selected from the group consisting of:

-continued

(13)
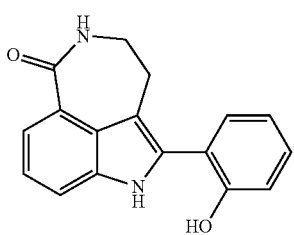

(14)
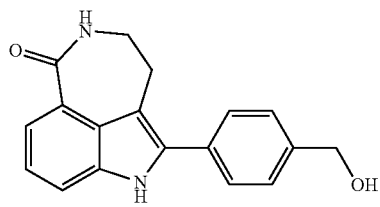

(15)
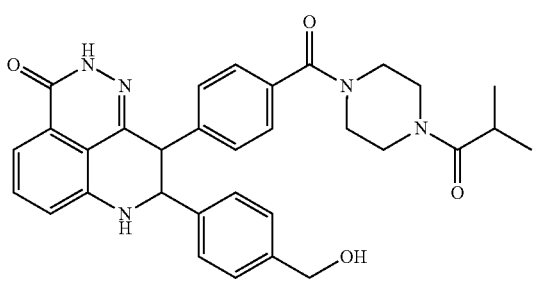

(16)
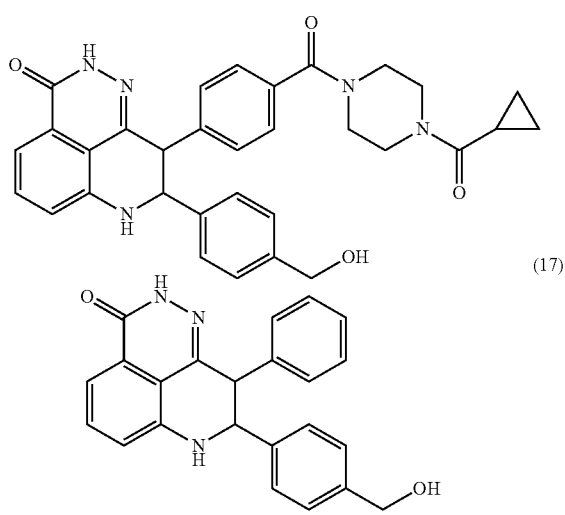

(17)

and the PARP inhibitor is bound to the polymeric compound or to the aspartic acid residue through an ester bond derived from the hydroxy group of the PARP inhibitor and the carboxy group of the polymeric compound or of the aspartic acid residue;

$R_4$ represents an aspartic acid residue and/or an aspartic acid imide residue;

$R_5$ represents $N(R_6)CONH(R_7)$; and $R_6$ and $R_7$, which are the same or different from each other, represent (C3-C6)branched or cyclic alkyl group, or (C1-C5)branched or linear alkyl group which is unsubstituted or substituted with a tertiary amino group.

2. The polymeric compound according to claim 1, wherein $R_1$ is methyl or ethyl group;

A is ethylene or trimethylene group;

$R_2$ is acetyl or propionyl group;

both $R_6$ and $R_7$ are cyclohexyl or isopropyl group;

the ratio of d compared to d+e+f+g+h is 5-40%;

the ratio of e compared to d+e+f+g+h is 5-80%;

the ratio of f compared to d+e+f+g+h is 0-60%;

the ratio of g compared to d+e+f+g+h is 5-40%; and the ratio of h compared to d+e+f+g+h is 0-30%.

3. The polymeric compound according to claim 1, wherein the PARP inhibitor is 2-(4-hydroxyphenyl)-1H-benzimidazole-4-carboxamide or 2-(4'-hydroxyphenyl)-3,4,5,6-tetrahydro-1H-azepino[5,4,3-cd]indol-6-one.

4. The polymeric compound according to claim 1, wherein the PARP inhibitor is 2-(4'-hydroxymethylphenyl)-3,4,5,6-tetrahydro-1H-azepino[5,4,3-cd]indol-6-one or 4-[4-fluoro-3-([1,4]diazepane-1-carbonyl-4-hydroxyethyl)benzyl]-2H-phthalazin-1-one.

5. An anticancer agent comprising the polymeric compound according to claim 1 as an active ingredient.

* * * * *